(12) United States Patent
Fang et al.

(10) Patent No.: US 9,532,704 B2
(45) Date of Patent: Jan. 3, 2017

(54) OPTICALLY GUIDED FEEDING TUBE, CATHETERS AND ASSOCIATED METHODS

(71) Applicant: University of Utah Research Foundation, Salt Lake City, UT (US)

(72) Inventors: John Fang, Salt Lake City, UT (US); Mark Adams, Salt Lake City, UT (US); Dylan McCreedy, St. Louis, MO (US); Tim Nieman, North Salt Lake, UT (US); Omar Galiano, Fairfax, VA (US); Brett Richins, Layton, UT (US); Shawn Andrus, Big Rapids, MI (US)

(73) Assignee: UNIVERSITY OF UTAH, Salt Lake City, UT (US)

( * ) Notice: Subject to any disclaimer, the term of this patent is extended or adjusted under 35 U.S.C. 154(b) by 742 days.

(21) Appl. No.: 13/752,150

(22) Filed: Jan. 28, 2013

(65) Prior Publication Data
US 2014/0039253 A1 Feb. 6, 2014

Related U.S. Application Data

(63) Continuation of application No. 12/756,129, filed on Apr. 7, 2010, now Pat. No. 8,361,041.
(Continued)

(51) Int. Cl.
*A61B 1/04* (2006.01)
*A61B 1/273* (2006.01)
(Continued)

(52) U.S. Cl.
CPC ............ *A61B 1/04* (2013.01); *A61B 1/00045* (2013.01); *A61B 1/00082* (2013.01);
(Continued)

(58) Field of Classification Search
CPC ... A61B 1/04; A61B 1/00045; A61B 1/00165; A61B 1/015; A61B 1/042; A61B 1/07; A61B 1/273; A61B 1/2733; A61B 1/2736; A61B 1/06; A61J 15/0003; A61J 15/0007; A61J 15/0046; A61J 15/0049; A61J 15/0069; A61J 15/0073; A61J 15/0015; A61M 25/01; A61M 25/0147
(Continued)

(56) References Cited

U.S. PATENT DOCUMENTS

| 4,253,448 A | 3/1981 | Terada |
| 4,290,421 A | 9/1981 | Siegmund |

(Continued)

FOREIGN PATENT DOCUMENTS

| EP | 0400369 | 12/1990 |
| JP | 7-136108 | 5/1995 |

(Continued)

OTHER PUBLICATIONS

International Search Report from related PCT Patent Application No. PCT/US2010/030429, Jan. 17, 2011.
(Continued)

*Primary Examiner* — Manuel Mendez
(74) *Attorney, Agent, or Firm* — Stoel Rives LLP

(57) ABSTRACT

The present invention provides devices and methods for safe, easy and cost effective means of placing and verifying proper placement of nasogastric and nasoenteric feeding tubes. Specifically, an integrated feeding device including a tube operable to deliver a nutritional and/or medicinal substance to the gastrointestinal tract, an optical system including a light source, flexible optical fibers or a camera, and a lens, and a steering system is disclosed. The components of the system, namely the optical system and the steering system, may be integrated into the tube.

13 Claims, 16 Drawing Sheets

Related U.S. Application Data

(60) Provisional application No. 61/168,144, filed on Apr. 9, 2009.

(51) Int. Cl.
| | |
|---|---|
| A61B 1/00 | (2006.01) |
| A61B 1/015 | (2006.01) |
| A61B 1/07 | (2006.01) |
| A61B 1/06 | (2006.01) |
| A61J 15/00 | (2006.01) |
| A61M 25/01 | (2006.01) |

(52) U.S. Cl.
CPC .......... *A61B 1/00165* (2013.01); *A61B 1/015* (2013.01); *A61B 1/042* (2013.01); *A61B 1/07* (2013.01); *A61B 1/273* (2013.01); *A61B 1/2733* (2013.01); *A61B 1/2736* (2013.01); *A61J 15/0003* (2013.01); *A61J 15/0007* (2013.01); *A61J 15/0046* (2013.01); *A61J 15/0049* (2013.01); *A61J 15/0069* (2013.01); *A61J 15/0073* (2013.01); *A61B 1/06* (2013.01); *A61J 15/0015* (2013.01); *A61M 25/01* (2013.01); *A61M 25/0147* (2013.01)

(58) Field of Classification Search
USPC ....... 600/104, 112, 141, 564, 118, 156, 109; 604/30, 264
See application file for complete search history.

(56) References Cited

U.S. PATENT DOCUMENTS

| | | | |
|---|---|---|---|
| 4,315,509 A | | 2/1982 | Smit |
| 4,356,824 A | * | 11/1982 | Vazquez ............. A61J 15/0015 604/119 |
| 4,384,584 A | | 5/1983 | Chen |
| 4,580,551 A | | 4/1986 | Siegmund et al. |
| 4,601,284 A | | 7/1986 | Arakawa et al. |
| 4,615,332 A | | 10/1986 | Buess et al. |
| 4,701,910 A | | 10/1987 | Ulug |
| 4,759,346 A | | 7/1988 | Nakajima |
| 4,769,014 A | | 9/1988 | Russo |
| 4,781,677 A | * | 11/1988 | Wilcox ................. A61B 17/22 600/561 |
| 4,809,680 A | | 3/1989 | Yabe |
| 4,844,071 A | | 7/1989 | Chen et al. |
| 4,860,731 A | | 8/1989 | Matsuura |
| 4,911,148 A | | 3/1990 | Sosnowski et al. |
| 4,998,527 A | | 3/1991 | Meyer |
| 5,049,070 A | * | 9/1991 | Ademovic ............. A61B 1/042 348/66 |
| 5,085,216 A | | 2/1992 | Henley, Jr. et al. |
| 5,116,317 A | | 5/1992 | Carson, Jr. et al. |
| 5,131,380 A | | 7/1992 | Heller et al. |
| 5,159,446 A | | 10/1992 | Hibino et al. |
| 5,167,220 A | | 12/1992 | Brown |
| 5,441,503 A | | 8/1995 | Considine et al. |
| 5,456,251 A | | 10/1995 | Fiddian-Green |
| 5,571,089 A | * | 11/1996 | Crocker ............. A61M 25/1011 604/103.01 |
| 5,577,992 A | | 11/1996 | Chiba et al. |
| 5,630,795 A | | 5/1997 | Kuramoto et al. |
| 5,658,238 A | | 8/1997 | Suzuki et al. |
| 5,665,064 A | | 9/1997 | Bodicky et al. |
| 5,807,314 A | | 9/1998 | Ross et al. |
| 5,855,549 A | | 1/1999 | Newman |
| 5,989,231 A | * | 11/1999 | Snow .................. A61B 1/2736 600/109 |
| 5,999,678 A | | 12/1999 | Murphy-Chutorian et al. |
| 6,015,400 A | | 1/2000 | Ross et al. |
| 6,030,360 A | | 2/2000 | Biggs |
| 6,322,495 B1 | | 11/2001 | Snow et al. |
| 6,322,498 B1 | | 11/2001 | Gravenstein et al. |
| 6,447,444 B1 | | 9/2002 | Avni et al. |
| 6,461,569 B1 | | 10/2002 | Boudreaux |
| 6,464,686 B1 | | 10/2002 | O'Hara et al. |
| 6,694,979 B2 | | 2/2004 | Deem et al. |
| 6,709,388 B1 | | 3/2004 | Mosse et al. |
| 6,712,757 B2 | | 3/2004 | Becker |
| 6,802,809 B2 | | 10/2004 | Okada |
| 6,994,667 B2 | | 2/2006 | Singh |
| 7,169,105 B2 | | 1/2007 | Iwasaka et al. |
| 7,220,253 B2 | | 5/2007 | Kantsevoy et al. |
| 7,615,002 B2 | | 11/2009 | Rothweiler et al. |
| 7,615,003 B2 | | 11/2009 | Stefanchik et al. |
| 7,648,457 B2 | | 1/2010 | Stefanchik et al. |
| 7,757,695 B2 | | 7/2010 | Wilson |
| 2002/0058859 A1 | * | 5/2002 | Brommersma .......... A61B 1/12 600/156 |
| 2003/0125601 A1 | | 7/2003 | Schock et al. |
| 2004/0215061 A1 | | 10/2004 | Kimmel et al. |
| 2006/0084838 A1 | | 4/2006 | Takuma |
| 2006/0229497 A1 | | 10/2006 | Toyama |
| 2006/0258903 A1 | | 11/2006 | Stefanchik et al. |
| 2006/0258904 A1 | | 11/2006 | Stefanchik et al. |
| 2006/0258907 A1 | | 11/2006 | Stefanchik et al. |
| 2006/0258955 A1 | | 11/2006 | Hoffman et al. |
| 2006/0259010 A1 | | 11/2006 | Stefanchik et al. |
| 2007/0015968 A1 | | 1/2007 | Shelnutt |
| 2007/0038027 A1 | | 2/2007 | Miyagi et al. |
| 2007/0038031 A1 | | 2/2007 | Miyagi et al. |
| 2007/0167683 A1 | | 7/2007 | Couvillon |
| 2007/0203393 A1 | | 8/2007 | Stefanchik |
| 2007/0260113 A1 | | 11/2007 | Otawara |
| 2007/0260119 A1 | | 11/2007 | Otawara |
| 2007/0260120 A1 | | 11/2007 | Otawara |
| 2007/0270651 A1 | | 11/2007 | Gilad et al. |
| 2008/0027408 A1 | | 1/2008 | Wilson et al. |
| 2008/0177144 A1 | | 7/2008 | Otawara |
| 2008/0208006 A1 | | 8/2008 | Farr |
| 2008/0228066 A1 | | 9/2008 | Waitzman |
| 2008/0269557 A1 | | 10/2008 | Marescaux et al. |
| 2009/0062772 A1 | | 3/2009 | Wakeford et al. |
| 2009/0082630 A1 | | 3/2009 | Tulley |
| 2009/0275825 A1 | | 11/2009 | Thomas |
| 2009/0318757 A1 | | 12/2009 | Singh |
| 2009/0318798 A1 | | 12/2009 | Singh et al. |
| 2010/0068320 A1 | | 3/2010 | Kuwabara |
| 2010/0094116 A1 | | 4/2010 | Silverstein |

FOREIGN PATENT DOCUMENTS

| | | |
|---|---|---|
| JP | 09-286806 | 10/1997 |
| WO | WO 2005-099376 | 10/2005 |
| WO | WO 2009-108854 | 9/2009 |

OTHER PUBLICATIONS

International Search Report from related PCT Patent Application No. PCT/US2011/066324, Jul. 2, 2012.
Preliminary Amendment in U.S. Appl. No. 13/332,277 dated Dec. 20, 2011.
Preliminary Amendment and Response to Notice of Missing Part in U.S. Appl. No. 13/332,277 dated Dec. 20, 2012.
Response to Restriction/Election Requirement in U.S. Appl. No. 13/332,244 dated Apr. 22, 2014.
Restriction/Election Requirement issued in U.S. Appl. No. 13/332,244 on Nov. 22, 2013.
Supplementary European Search Report in PCT/US2010/030429.
Office Action issued in U.S. Appl. No. 13/332,244 on Jul. 17, 2014.
Office Action issued in U.S. Appl. No. 13/332,277 on May 22, 2015.
Notice of Allowance issued in U.S. Appl. No. 13/332,244 on May 18, 2015.
Response to Office Action in U.S. Appl. No. 13/332,244, filed Jan. 14, 2015.
Response to Restriction/Election Requirement in U.S. Appl. No. 13/332,277 dated Feb. 10, 2015.
Restriction/Election Requirement issued in U.S. Appl. No. 13/332,277 dated Sep. 11, 2014.

(56) References Cited

OTHER PUBLICATIONS

Applicant Initiated Interview Summary mailed Sep. 19, 2012 in U.S. Appl. No. 12/756,129.
Applicant's Amendment under 37 C.F.R. §1.312 filed Dec. 13, 2012 in U.S. Appl. No. 12/756,129.
Applicant's Interview Summary, filed Oct. 19, 2012 in U.S. Appl. No. 12/756,129.
Corrected Notice of Allowance mailed Mar. 30, 2015 in U.S. Appl. No. 13/332,244.
Response to Rule 312 Communication mailed Dec. 27, 2012 in U.S. Appl. No. 12/756,129.
Office Action issued in U.S. Appl. No. 12/756,129 on May 9, 2012.
Office Action issued in U.S. Appl. No. 12/756,129 on Oct. 11, 2012.
Notice of Allowance issued in U.S. Appl. No. 12/756,129 on Nov. 13, 2012.
Response to Office Action in U.S. Appl. No. 12/756,129, filed Aug. 2, 2012.
Response to Office Action in U.S. Appl. No. 12/756,129, filed Nov. 2, 2012.
Response to Restriction/Election Requirement in U.S. Appl. No. 12/756,129, filed Feb. 17, 2012.
Restriction/Election Requirement issued in U.S. Appl. No. 12/756,129 on Jan. 18, 2012.

\* cited by examiner

OPTICALLY GUIDED FEEDING TUBE, CATHETERS AND ASSOCIATED METHODS

RELATED APPLICATIONS

The present application claims the benefit of U.S. Provisional Patent Application No. 61/168,144, filed Apr. 9, 2009, which is expressly incorporated herein in its entirety.

FIELD OF THE INVENTION

The present invention relates to devices and methods associated with feeding tubes and other catheters which enable directed placement and confirmation of correct placement using optics to view the interior anatomy of the gastrointestinal tract. In some aspects, the invention relates to nasogastric, nasoenteric and percutaneous feeding tubes and the placement of such tubes. In other aspects, the present invention relates to catheters for drainage and/or removal of fluids. Accordingly, the present invention involves the fields of biology, physics, material science, and engineering.

BACKGROUND

Nasogastric and nasoenteric feeding tubes play a crucial role in treating patients having a compromised oral intake. Placement of these feeding tubes is routinely performed in a number of clinical settings throughout the United States including emergency rooms, hospital wards and intensive care units totaling greater than 1.2 million tubes annually. The most common method of feeding tube placement currently is blind placement, which is estimated to comprise 70 percent of feeding tube placements. Blind placement is performed at the bedside by nurses or other hospital staff, and entails blindly inserting the feeding tube down the nose, through the esophagus and into the stomach or small intestine.

Because the nurse or other hospital staff cannot see the distal end of the feeding tube during advancement, the feeding tube can be incorrectly positioned during the process. In extreme cases, the distal end of the feeding tube may pass into the cranium and into the patient's brain, while the nurse or other practitioner continues advancing the feeding tube believing that it is properly entering the gastrointestinal tract.

More commonly, misplacement of the feeding tube results in other serious complications including lung placement or puncture or esophageal puncture. It is estimated that 3.2 percent of all blind nasoenteric feeding tube placements result in the feeding tube being disposed in the lung. In approximately 1.2 percent of placements, the patient will suffer a punctured lung. In 0.5 percent of cases, the patient will die as a result of the procedure. It is estimated that in intensive care units alone, up to six thousand patients die each year from improperly placed feeding tubes.

Additionally, providing any feeding solution through the feeding tube into the lungs results in pneumonia with increased morbidity and mortality. Thus, it is critical to ensure that there has been proper placement of the feeding tube. Unfortunately, many common methods for during so leave patients at substantial risk.

Proper placement of the tube is verified using a variety of tests, including chest x-ray, pH tests, auscultation, or fluoroscopy. However, these tests only attempt to confirm position after placement when complications may have already occurred. For example, if fluoroscopy or X-ray confirms that the feeding tube is actually disposed in the lung, it does so only after the possibility of lung puncture or other damage to the lung tissue. Additionally, while X-ray imaging and fluoroscopy are often used, both only provide a two dimensional indication of location, i.e. placement below the diaphragm. In multiple instances, confirmation of placement has been given when the feeding tube had actually passed through the lung and along the diaphragm, rather than being disposed in the gastrointestinal tract. Moreover, X-ray or fluoroscopic confirmation does not clearly confirm placement in the small bowel rather than the stomach. Small bowel placement is generally preferred to prevent the risk of aspirating feeding solution.

Additionally, some of these techniques have additional limitations and drawbacks. For example, fluoroscopic exams and X-Ray verification can cost $400 or more and can expose the patient and the practitioner to harmful radiation. If a patient is pregnant, or a child, exposure to such radiation is highly undesirable. Additionally, the use of such verification procedures significantly prolongs the period of time that a patient must wait after a feeding tube is placed before feeding can begin. Because of this, the average time from ordering feeding tube placement to confirmation of placement and beginning of feeding is 22-26 hours. If the tube is placed improperly, the wait to begin feeding can take even longer as the process must be repeated. During this time, the patient is unable to obtain nourishment and any medications which may be delivered via a feeding tube.

Another complication which is common with patients receiving a patient tube is that the patients are often not coherent. The patient may be partially sedated or may be delirious. Thus, it is not uncommon for a patient to pull out a feeding tube which has previously been placed. This requires repetition of the procedure, again subjecting the patients to the risks set forth above. Thus, a simpler, safer method for placing feeding tubes would be highly desirable.

An alternate method for placement and verification of a feeding tubes is by use of an endoscope. Typically an endoscope is inserted into the mouth of the patient and advanced down until the endoscope has passed through the esophagus and at least into the stomach, and preferably through the pyloric sphincter and into the duodenum. In some applications, a guidewire is advanced to the proper location and the endoscope is removed. The guidewire is then manipulated to move it from the oral placement to a nasal placement, and a feeding tube is advanced along the guidewire into the desired location.

In other applications, the feeding tube is carried in a working channel (or along the side) of the endoscope. The feeding tube is sufficiently long that once the feeding tube has been placed, the endoscope can be removed over the feeding tube. The feeding tube is then cut and an appropriate adapter attached for feeding.

While placement and verification using an endoscope is advantageous, it also has several drawbacks. First using an endoscope usually takes considerable skill and is typically performed by physicians, often requiring a wait until a properly trained physician is available to place the feeding tube. Second, because the endoscope is typically placed through the mouth, an additional procedure must be used if the feeding tube is to be used nasoenterically. This involves advancing a structure through the nose and out the mouth, securing the end of the feeding tube (or a guidewire) to the structure, and then pulling the structure and the end of the feeding tube through the nose. Third, the use of an endoscopic procedure requires re-sterilization of the endoscope after each use. Lastly the procedure usually requires conscious sedation which increases the risk and cost of the procedure.

Each of the above-referenced methods for placing a feeding tube also has the problem of subsequently confirming proper placement of the feeding tube. As a patient moves, the distal end of the feeding tube can work its way out of the intestine and coil in the stomach. Depending on the particular concerns regarding the patient, it may be necessary to periodically confirm that the feeding tube is placed properly. This can require additional x-ray, pH tests, auscultation, or fluoroscopy, or the use of another endoscope to ensure that the feeding tube is properly placed. Each of these methods for confirming placement has the drawbacks mentioned above.

Accordingly, it would be desirable to provide a feeding tube which can be placed more conveniently and which can be used to confirm placement without the need for radiation or other traditional confirmation methods. Additionally, it would be advantageous if such a feeding tube and method of use could be accomplished by nurses and other medical staff.

In addition to nasogastric and nasoenteric feeding tubes, an improved jejunual extension tube in percutaneous gastrojejunal feeding tubes (PEGJ) that utilized direct visualization for advancement, placement and confirmation would be useful. Presently for PEGJ tubes the jejunal extension tube must be threaded through the existing gastrostomy tube or stoma into the small bowel. This is done using fluoroscopy or endoscopy to advance a wire into the small intestine and then a jejunal feeding tube is passed over the wire into the small intestine (jejunum). A jejunal extension tube with direct visualization and/or steering mechanism could perform the same task without the drawbacks of using endoscopy or fluoroscopy as noted previously.

In addition to improved feeding tubes, there are other situations in which prolonged visualization and access for irrigation/infusion and drainage would be beneficial. For example, in pancreatobiliary infections, it is not uncommon for the common bile duct (or associated duct) to become blocked and restrict flow of fluid into the duodenum. An endoscope or other catheter based method is typically used to place a shunt or stent in the pancreatic duct or the common bile duct to allow proper drainage of pus from the pancreatobiliary ducts through the common bile duct into the duodenum. Once the situation has been alleviated, an endoscope or other device may be advanced back into the duodenum to remove the shunt or stent. Of course, it is often difficult to tell if the situation has been fully alleviated, if the device has become misplaced, or if the symptoms have simply been reduced.

In these procedures, as well as others in the body, it may be advantageous to provide continued viewing capacity both to ensure proper placement of the structure used for drainage, and to allow medical personnel to get a view of the affected area to determine whether and how quickly healing and/or drainage is taking place. In these clinical situations such a device can replace or assist fluoroscopy and/or endoscopy for guidance, placement, confirmation and re-confirmation. In addition, such an indwelling device can be used to drain pus or other bodily fluids from body cavities as well as provide a conduit for irrigation and infusion of medications including antibiotics.

SUMMARY OF THE INVENTION

Accordingly, the present invention provides devices and methods for safe, easy, and cost effective means of placing and verifying proper placement of feeding tubes and/or drainage tubes in a body. The methods may simplify placement and allow medical personnel to properly place and confirm initial placement and to reconfirm placement whenever necessary.

Specifically, in accordance with one aspect of the invention, an integrated feeding tube device is provided. The device includes a tube operable to deliver nutritional and/or medicinal substance to the gastrointestinal tract and an optical system (which may include a light source, such as flexible optical fibers and an image transmitting device such as optical fibers attached to a lens, or a miniature camera).

The tube may also include a steering system. Thus, the components of the system, namely the optical system and the steering system, may all be integrated into the feeding tube.

In another aspect of the invention, a method of placing a feeding tube inside a gastrointestinal tract of a subject is provided. The method includes providing an integrated feeding tube device, such as the feeding tube described above, and inserting a distal end of an integrated feeding tube device into the nasal or oral passage of a subject. As the integrated feeding tube is advanced through the nasal passages and through the pharynx, the optical system is used to view the tissues adjacent the feeding tube to ensure that the feeding tube is directed down the esophagus and not past the larynx and into the trachea and bronchi where the feeding tube can puncture the lung. Additionally, the optical system can be used to ensure that the tip of the catheter does not catch against the sides of the esophagus, potentially damaging tissue.

While the distal end of the feeding tube may be left in the stomach, it is often preferred to advance the distal end past the stomach, through the pyloric sphincter and into the duodenum or jejunum. This minimizes the risk of reflux and bypasses the stomach which often does not function well in certain clinical situations.

Because the optical system enables a physician or nurse to guide the feeding tube and confirm that the distal end of the feeding tube is properly placed in the gastrointestinal tract, the procedure will typically take less time (typically $¼^{th}$ or less) than blind placement, thereby reducing patient discomfort. Additionally, during placement with optical confirmation the complications of lung placement or puncture, and cranial placement can be summarily avoided. Finally, once the placement of the distal end is confirmed, the feeding tube may be used to deliver a feeding solution and any medication necessary to the patient. Thus, instead of waiting 24 hours or more for radiology, etc., to confirm placement, feeding may begin within half an hour of initial placement of the feeding tube.

In accordance with one aspect of the invention, a control unit, which may include an image viewing device, such as a display screen, and a steering element can be used during placement. The control unit is removably attachable from the feeding tube. As soon as placement of the feeding tube is confirmed, the control unit can be removed and may be used for additional placements or confirmation of additional feeding tubes.

In accordance with another aspect of the invention, the control unit can be reattached to the feeding tube. If, for example, a physician wishes to reconfirm placement of the distal end of the feeding tube, the control unit need merely be reattached to the feeding tube and the image checked on the display screen. If the distal end of the feeding tube remains in a desired location along the gastrointestinal tract, the control unit is removed and feeding continued. If, however, the feeding tube has changed position to an undesired location, the control unit can be used to re-position the feeding tube to the desired location. Unlike conventional endoscopic verification, there is no need to advance a sterilized endoscope back down the patient's throat, and unlike fluoroscopy or x-ray, the patient is not subjected to any additional radiation.

With the control unit detached from the feeding tube, the feeding tube can be used similarly to conventional feeding tubes. However, whenever medical personnel wish to ensure placement of the feeding tube or observe tissue adjacent the distal end of the feeding tube, the control unit is simply reattached to the feeding tube, thereby providing a visual confirmation of placement. Thus, the feeding tube can be used both for feeding and for observing portions of the gastrointestinal tract.

In accordance with another aspect of the invention, the optical system is provided with a flush lumen which can be used to clean the distal end of the optical system to improve viewing. Solution, air or some other fluid may be put through the flush lumen to improve viewing. The flush lumen may be formed in the same lumen as carrying the optics system, thereby allowing the optics system to be cleaned independent of flushing the lumen used to deliver enteral nutrition.

In accordance with yet another aspect of the present invention, the optical system can be disposed in the lumen so as to be focused toward the long axis of the feeding tube to facilitate cleaning, reduce potential damage to the lens of the optical system and to improve the view provided by the optical system in the feeding tube.

In accordance with still another aspect of the invention, a catheter can be provided with an integrated optical system and a flow channel to enable the catheter to act as a shunt to allow fluid flow from one part of the body to another part of the body. For example, the distal end of the catheter can be advanced through the nose and esophagus, through the stomach and into the pancreatic or biliary duct. The optical system allows viewing of the tissue of concern, ie. the pancreas or bile duct, and enables a physician to check the status by, for example, observing whether pus is still being emitted from the pancreatobiliary ducts. Once the pancreas, common bile duct, etc., has returned to normal, the catheter can be withdrawn. Thus, the patient is subjected to only one invasive placement and the physician is provided with the ability to view the affected region at any desired time.

In accordance with still yet another aspect of the invention, a feeding tube is provided which has a tube with an optical system disposed in the feeding lumen. The optical system remains in place while the feeding tube is placed nasoenterically (or oroenterically) so as to enable the medical personnel to observe advancement of the feeding tube in the gastrointestinal tract. Once the feeding tube is placed into the desired position, the tube containing the optical system can then be removed and the lumen used for enteral feeding, etc. If subsequent confirmation of the position of the feeding tube is desired, the feeding lumen is flushed and an optical system tube may be readvanced down the feeding lumen and allow visual confirmation. The optical feeding tube, however, is much cheaper than use of an endoscope and can be disposed of rather than resterilized. Additionally, the optical feeding tube does not require oral passage of an endoscope and does not require the use of a guidewire.

In accordance with still yet another aspect of the present invention, a feeding tube made in accordance with the principles of the present invention may be used as an improved jejunual extension tube in percutaneous gastrojejunal feeding tubes (PEGJ). The feeding tube provides direct visualization for advancement, placement and confirmation of placement in the small bowel, rather than using a guidewire and fluoroscopy or an endoscope to place the jejunal extension tube. With the optical system and steering, a feeding tube made in accordance with the present invention can perform the same task as conventional jejuna feeding tubes without the drawbacks of using endoscopy or fluoroscopy as noted previously.

In accordance with the present invention, the ease of placement is enhanced and the overall use of feeding tubes may be increased. For example, rather than requiring a patient to be transported to a hospital for placement of a feeding tube, a nurse at a nursing home to place a feeding tube in an elderly patient who was suffering from an illness which made it difficult to keep food down. Likewise, with very little training a pediatrician, nurse, or physician's assistant to place feeding tubes in a pediatric clinic where a child is suffering from the flu and cannot hold down liquids. Healthcare providers who can be trained to place this feeding tube include; physicians, physician assistants, nurses, nurse practitioners and registered dieticians.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Additional features and advantages of the invention will be apparent from the detailed description that follows, taken in conjunction with the accompanying drawings, which together illustrate, by way of example, features of the invention; and, wherein:

FIG. 4 shows an explosed, perspective view of an optically guided feeding tube system including a feeding tube and a control unit formed in accordance with another aspect of the present invention, while

Figure 1A:
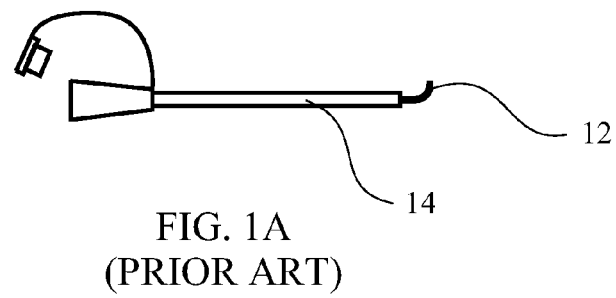
FIGS. 1A through 1C illustrate various components of devices used for placing feeding tubes in accordance with the prior art, including a feeding tube having a guide wire (FIG. 1A), an intubation tube with a guidewire (FIG. 1B) and a close-up of a curved end of a guidewire (FIG. 1C)

The drawings will be described further in connection with the following detailed description. Further, these drawings are not necessarily to scale and are by way of illustration only such that dimensions and geometries can vary from those illustrated.

DETAILED DESCRIPTION

Definitions

Before the present invention is disclosed and described, it is to be understood that this invention is not limited to the particular structures, process steps, or materials disclosed herein, but is extended to equivalents thereof as would be recognized by those ordinarily skilled in the relevant arts and by the terms set forth in the claims. It should also be understood that terminology employed herein is used for the purpose of describing particular aspects of the invention only and is not intended to limit the invention to the aspects or embodiments shown.

It must be noted that, as used in this specification and the appended claims, the singular forms "a," "an," and "the" may include plural referents unless the context clearly dictates otherwise. Thus, for example, reference to "an optical fiber" may include one or more of such optical fibers, and reference to "the lens" may include reference to one or more of such lenses.

As used herein, "subject" or "patient" refers to a mammal that may benefit from the devices and methods of the present invention. Examples of subjects include humans, and may also include other animals such as horses, pigs, cattle, dogs, cats, rabbits, and other land and aquatic mammals.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The Invention

An integrated feeding tube device is provided that can safely and effectively place and verify placement of the feeding tube in the gastrointestinal tract of the patient. The device may include a feeding tube operable to deliver a nutritional and/or medicinal substance to the gastrointestinal tract, a steering system used to help guide the feeding tube to the desired location in the gastrointestinal tract, and an optical system including structures to provide light into the gastrointestinal tract, and an optical system having image transmitting device such as flexible optical fibers and a lens or a camera for transmitting images of the gastrointestinal tract. Components of the system, namely the optical system and the steering system, may be all integrated into the feeding tube so as to enable directed placement of the feeding tube, confirmation of placement of the feeding tube and to enable repositioning of the distal end of the tube if necessary.

Feeding tubes as described herein can be any type of feeding tubes known, including, without limitation, nasogastric and nasoenteric tubes and percutaneous gastrostomy, percutaneous gastrojejunostomy and percutaneous jejunal feeding tubes. Such tubes can be made of any material known in the feeding tube industry. Generally any flexible plastic or polymeric material can be used. The feeding tube is generally hollow and capable of delivering nutritional, medicinal, or other oral agents to a subject. The diameter of the feeding tube can vary depending on the intended use, e.g. the characteristics of the subject or the duration of feeding tube use. For example, a tube intended for use with infants and small children will typically have a smaller diameter and delivery capacity than those intended for use with adults. Feeding tubes are well known in the art, and any such tube or tube configuration would be considered to be within the present scope.

The optical system of the integrated feeding tube device can include one or more light carrying members, which may include fiber optic fibers or other light conveying structures and optical transmission mechanisms such as optical fibers attached to one or more lenses or a miniature camera. Collectively, the components of the optical system function to deliver light to the distal end of the device, to provide the ability to visually observe an area around the distal end of the feeding tube during placement within the subject. This visual observation can aid a practitioner during placement of the device and in verifying proper placement of the device within the gastrointestinal tract. The resolution of images or video produced by the optical system can be of any level, provided sufficient resolution is obtained for a practitioner to be able to quickly and accurately identify the type of tissue, body lumen or cavity seen through the optical system. For example, it is desirable that a practitioner be able to quickly distinguish between the trachea and the esophagus, and most critically that the practitioner can ensure that the tissue being seen is not the bronchi or lung tissue.

While endoscopes usually provide high resolution because they are often used for closely examining tissue for diagnosis or carrying out procedures, it is not necessary for the feeding tube to provide high resolution. Although high resolution can be used, lower resolution images can be sufficient to verify proper placement of the integrated feeding tube device in the gastrointestinal tract and ensure that the feeding tube is not in the lungs.

The optical system can have depth of field range of from about 2 mm to about 100 mm, and can have a field of view of from about 30° to about 140°. In one embodiment, the optical system can have a field of view of from about 60° to about 125°.

When used, the optical fibers used in the optical system can be made of any material known in the art including, but not limited to silica, fluorozirconate, fluoroaluminate, chalcogenide, and plastic optical fibers such as polymethylmethacrylate, and the like. In one embodiment, the optical fibers can be made from polymethylmethacrylate. Additionally, the lenses of the optical system can be made from any material known in the lens art including, but not limited to silica and polymers such as polymethylmethacrylate. In one embodiment, the lenses can be made from gradient index polymethylmethacrylate. In the event a camera is used, a camera such as a cmos camera works well because the can be acquired in a diameter of about 1 mm and are not overly expensive. However, it will be appreciated that other cameras may be used.

One or more of the optical fibers (or some other structure) can transmit light for illuminating an area at the end of the integrated tube device, and one or more other optical fibers can carry the visual images from the end of the device to a viewing component which, as discussed below, may be formed as part of a control unit. In the alternative, a cable or wire could carry images from a camera. It will be appreciated that the present invention includes numerous different aspects which may stand alone or which may be used in combination. Thus, the presence of a feature in one of the figures is for illustration purposes and it will be appreciated that any of the devices shown in the drawings could include features shown in other drawings, but which have been omitted to keep the drawings readily understandable.

In one embodiment, at least one optical fiber(s) provides illumination at the distal end of the integrated feeding tube device of at least 800 Candelas. In another embodiment, at least one optical fiber(s) provides illumination at the distal end of the integrated feeding tube device of at least 1000 Candelas. In the alternative, or in conjunction, Infrared light may be used as cameras can be used to pick up multiple wavelengths of light, or a camera which provides images based solely on Infrared light may be used.

Figure 1B:
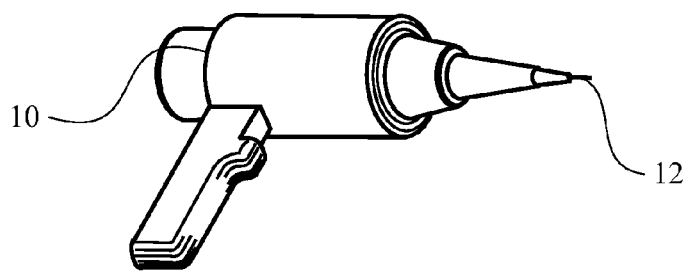
Figure 1C:
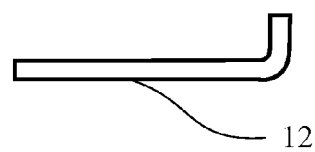

Turning momentarily to FIGS. 1A through 1C, there are shown prior art mechanisms for placing a feeding tube. One is an intubation device 10 (FIG. 1B) with a guidewire 12 extending therefrom which may be inserted into the mouth of a patient. The other is a nasoenteric feeding tube 14 (FIG. 1A) with a guidewire 12. FIG. 1C is a close-up of the curved end of a guidewire which can facilitated steering or placement. Such devices can be used for blind placement or with an endoscope. However, as will be explained below, the present invention has several marked advantages over blind and endoscopic placement of feeding tubes.

Figure 2A:
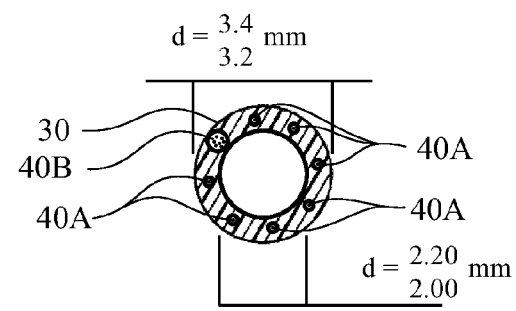
FIG. 2A is a cross-sectional view of a nasoenteric feeding tube formed in accordance with the principles of the present invention.

Turning now to FIG. 2A, there is shown a cross-sectional view of a feeding tube 30 having an optical system integrated into a wall of the feeding tube. In such an embodiment, optical fibers can be incorporated directly into the feeding tube 30 during manufacturing of the tube. Thus, optical fibers 40A and 40B are directly incorporated into the feeding tube wall. Fibers 40A (which may be for example 30 μm fibers or other sized fibers) are used for conveying light to the distal end of the feeding tube 30, while fibers 40B (which may be for example 0.5 mm fibers or other sized fibers) typically terminate in a lens and convey an image of the tissues adjacent the distal end of the feeding tube 30 to a viewing mechanism, such as an eyepiece or a monitor (not shown in FIG. 2A). It should be noted that the dimensions shown in FIG. 2A are merely exemplary, and are not to be seen as limiting the scope of the present invention.

While the feeding tube 30 may be used with an intubation device 10 and/or with a guide wire as shown in FIGS. 1A and 1B, in a presently preferred embodiment neither the intubation device 10 or a feeding tube having a guidewire is needed.

The lens and fibers 40a, 40B form an integrated optical system in the feeding tube 30. Images provided by the optical system can be viewed using an image viewing component (not shown in FIG. 1). The image viewing component can be any viewing device known in the art. In one embodiment, the image viewing component may include an eyepiece that is operably connected to the proximal end of the optical system 40b. By looking through the eyepiece a practitioner can view the image of tissue at the distal end 30A of the feeding tube 30. The practitioner can use the image to guide the feeding tube 30 to its desired location and/or verify the proper placement of the device based on the tissues observed.

The eyepiece can optionally include a lens that enhances or enlarges the image. While FIG. 1B shows an intubation device, one advantage of the present invention is that intubation is generally not necessary to properly place the feeding tube 30. Rather, a feeding tube 30 (or 130 as set forth below) may be placed more quickly and with less discomfort by advancing the feeding tube through the nasal canal and into the gastrointestinal tract without the need for radiological confirmation prior to feeding.

Figure 2B:
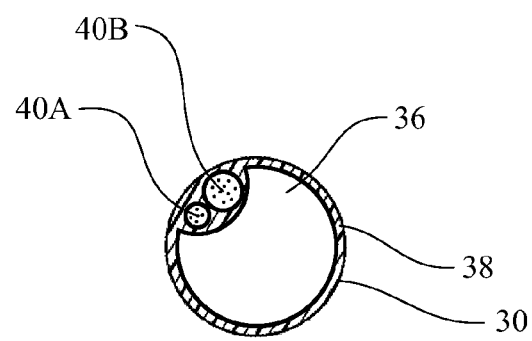
FIG. 2B is a cross-sectional view of an alternate configuration of a feeding tube formed in accordance with the present invention.

Another example of an embodiment of the optical fibers being incorporated directly into the feeding tube wall (or in a lumen formed in the wall) is shown in FIG. 2B. The feeding tube 30 includes three lumens (or channels within the outside wall). A first large lumen 36 is configured for delivery of feeding solution. Those familiar with enteral feeding solutions will appreciate that they can be somewhat viscous. Thus, it is desirable to have a lumen 36 which will facilitate the passage of the solution without making the feeding tube 30 uncomfortably large to pass through the patient's nasal canal. The other two lumens or formation in the exterior wall 38 are the light source 40A and the lens and optical fibers 40B which carry an image to the image viewing system discussed above. In the alternative, the optical fibers for lighting and viewing may be disposed in a common bundle (typically coaxially with optical viewing fibers surrounded by lighting fibers), or a lighting mechanism and camera could be used. The other lumen can then be used for steering in a manner discussed below.

Figure 3:
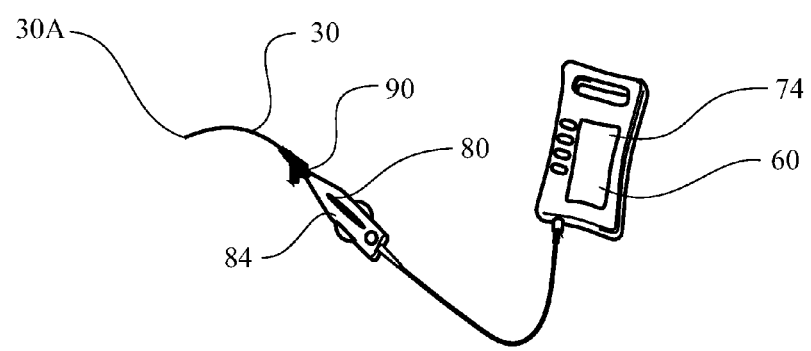
FIG. 3 is a perspective view of an optically guided feeding tube system in accordance with one aspect of the invention.

As shown in FIG. 3, the optical system 40 can be attached to a display, such as an electronic screen 74 that receives and displays the image from the optical fibers. The electronic screen 74 can be of any type or variety known in the art including, but not limited to small hand-held screens, computer monitors, televisions, etc. Also shown in FIG. 3 is a steering system 80 of the integrated feeding tube 30. By providing one or more wires in the feeding tube 30, a control unit 84 can be connected to the wire(s) which is capable of guiding the distal end of the integrated feeding tube device, thereby facilitating the placement of the device in the gastrointestinal tract. A variety of steering mechanisms are contemplated, all of which are intended to be within the present scope. In one embodiment, the steering system can include a wire that is capable of causing the distal end 30A of the integrated feeding tube 30 to bend when moved in one direction (typically longitudinally) and to straighten the feeding tube when moved in the opposite direction. In another embodiment, the steering system 80 can include a polymeric composition that can be manipulated to cause the distal end of the integrated feeding tube device to bend. The amount or degree of bend in the end of the integrated feeding tube device can be varied depending on the type of the steering system and the intended population for the device. In one embodiment, the steering system can provide a turning radius of about 2 cm to about 3 cm. Steering systems, such as those described above, can be operated by steering controls that are located at or near the proximal end of the integrated feeding tube device.

In another embodiment, the integrated feeding tube device can include a release coupling 90 to allow one or both of the image viewing component 60 and/or the steering control 80 to be disconnected from the feeding tube 30. Such a release coupling can be located on the feeding tube 30 such that the coupling remains external to the subject during placement of the tube. Releasing and removing the steering controls 80 and the image viewing components 60 allows the integrated tube to be less bulky, thus decreasing discomfort experienced by the subject while the tube is in position. Additionally, releasing and removing these systems allows the image viewing component 60 and steering control 80 to be reused. The ability to reuse these components of either with other feeding tubes, or with the same feeding tube 30 at a later time can substantially reduce the costs associated with the device and its use as compared to endoscopes and other means of confirming the placement of the feeding tube 30.

In some embodiments it may also be important that the feeding tubes of the present invention have couplings that properly articulate with standard feeding tube adapters. These standard adapters are used to couple the feeding tubes to feeding sets that are used to feed subjects or to deliver medicaments to subjects. In such a case, a feeding tube of the present invention can be placed in the subject, the steering and image viewing systems 80 and 60, respectively, can be decoupled, and feeding tube 30 can be coupled to a feeding set using a standard adapter.

In another embodiment of the invention, a method of placing a feeding tube inside a gastrointestinal tract of a subject is provided. The method includes providing an integrated feeding tube 30, such as described above, and inserting a distal end of an integrated feeding tube device into the nasal passage of a subject. The integrated feeding tube 30 is then positioned inside the gastrointestinal tract of the subject, such as by using the steering system 80 of the integrated feeding tube. After positioning of the integrated feeding tube 30, proper placement in the gastrointestinal tract of the subject can be visually verified by using the optical system 40B and the visualization component 60. It should be noted that the steering and optical system located within the feeding tube can increase the stiffness of the tube, thus facilitating tube placement in the subject.

Once placed, the feeding tubes 30 of the present invention can be typically maintained in the gastrointestinal tract for a period of up to 30 days. In some cases, the feeding tubes can be maintained for even longer periods of times. Removal of the integrated feeding tubes 30 of the present invention can be accomplished through the known methods in the art.

As with all feeding tubes, the integrated feeding tube devices of the present invention can be subject to frictional resistance during placement. In order to reduce frictional forces on the device, it can be desirable to lubricate the device prior to its placement in the subject. Biocompatible lubricants that can be used are well known in the art and include those that are currently used in feeding tube placement and endoscopy.

One distinct advantage of feeding tubes 30 of the present invention is that the optical system 40B can be used throughout the life of the feeding tube. At any time a practitioner wishes to confirm placement of the distal end 30A of the feeding tube 30 or wishes to view tissue in the gastrointestinal tract adjacent the distal end of the feeding tube, he or she need only reattach the image viewing system 60 and observe. With prior art feeding tubes, x-ray, fluoroscopy or other viewing methods that are both expensive and time consuming must be used. Additionally, the patient is exposed to additional radiation.

Figure 4:
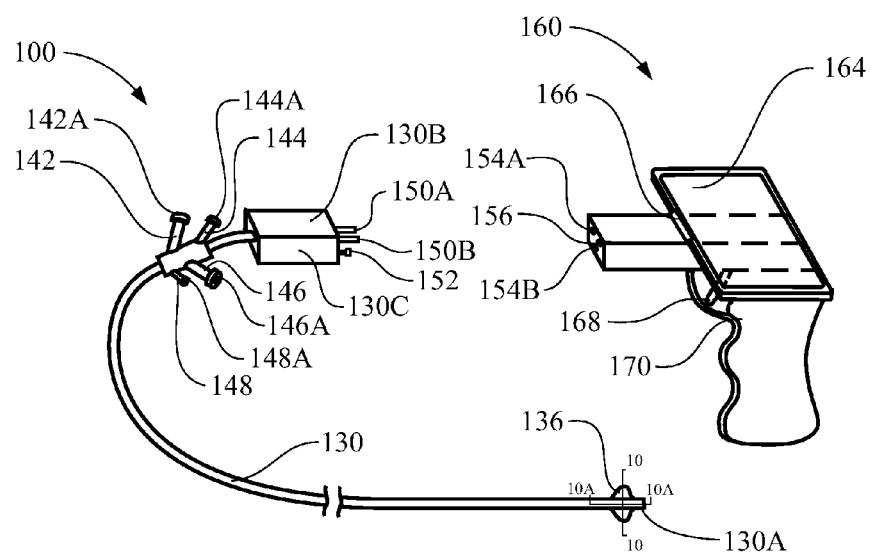

Turning now to FIG. 4, there is shown a perspective view of an optically guided feeding tube system, generally indicated at 100 formed in accordance with another aspect of the present invention. The feeding tube system 100 includes a feeding tube 130. At a distal end 130A the feeding tube 130 includes a port through which feeding solution, medication, or the like can be delivered to the gastrointestinal tract, and one or more openings through which light can be directed against tissue in the gastrointestinal tract and images thereof communicated to a proximal end 130B of the feeding tube 130.

Disposed adjacent the distal end 130B of the feeding tube 130 is an anchoring device 136. The anchoring device 136 can be a balloon, a coil, a stent or other structure which helps to hold the distal end 130A of the feeding tube 130 in the desired location in the gastrointestinal tract.

Disposed adjacent the proximal end 130B are a plurality of ports 142, 144, 146 and 148. Port 142 has a coupling or adapter 142A for attachment to an enteral feeding solution line and communicates with the feeding lumen in the feeding tube. Port 144 is disposed adjacent thereto and may include a coupling or adapter 144A configured to receive a syringe or other fluid source which is used to periodically flush the feeding lumen. Port 146 is provided to flush another lumen of the feeding tube 130 so as to clean the optical system as will be explained in additional detail below and may include a coupling or adapter 146A configured for receiving a syringe, etc. Port 148 may be provided to inflate the anchoring device 136 when such is a balloon, and may also have a coupling or adapter 148A configured to receive a syringe, etc.

As shown in FIG. 4, a feeding tube adapter 130c is disposed at the proximal end 130B of the feeding tube 130. The adapter 130c may have a plurality of projections which are used to operate the visualization and steering capabilities of the feeding tube 130. Projection 150A comprises a portion of the optical system (typically fiberoptic fibers) which transmit light through the distal end 130b. To effectuate the transmission of light, the fiber optic fibers 150A (or other transmission medium) engage an opening 154A in a control unit, generally indicated at 160. Inside the control unit is a light source which is conveyed through the optical system to cast light on tissue in the gastrointestinal tract. The optical system may provide concentric orientation or parallel orientation between transmission of light and images whether by fibers or by a camera, etc.

The second projection 150B engages an opening 154B in the control unit 160 and are disposed in alignment with a camera or other source for converting images. It will be appreciated that in a presently preferred embodiment, the projection 150B may be fiber optic fibers, but other transmission mediums can be used, such as a cable attached a camera in the feeding tube. Image conveyed to the control unit 160 can be displayed on an image viewer, such as a video display screen 164. While nearly any viewable size may be used, a 2×3 inch (5×7.6 cm) video screen is presently preferred as it is large enough to clearly see the tissue at the distal end 130A of the feeding tube 130, but can be kept immediately adjacent the feeding tube and other controls to prevent the practitioner from having to look away from the feeding tube while it is being advanced. Additionally, the screen can be pivotably attached by an attachment member 166 to the control unit to enable it to be pivoted into a position most comfortable for the practitioner.

The adapter 130c may also include a cable 152 which projects outwardly therefrom. The cable 152 can nest in an opening 156 in the control unit 160. A steering mechanism, such as a trigger 168 may be moved backward or forward to advance the cable toward or away from the distal end 130A of the feeding tube 130. As will be explained below, this enables the bending or straightening of the distal end 130A of the feeding tube 130 and facilitates advancement of the feeding tube through the gastrointestinal tract.

The control unit 160 may also include a handle portion 170. The handle portion 170 gives the practitioner an ergonomic structure with which to push the feeding tube 130 forward. It also facilitates twisting the feeding tube 130 if necessary for proper advancement.

Figure 4A:
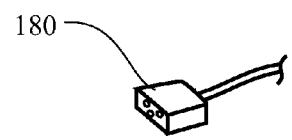
FIG. 4A shows an alternate adapter for a control unit.

While the control unit 160 is desirable for placement, if the patient has a condition that suggests frequent monitoring of the gastrointestinal tract, the control unit 160 could be removed and the adapter 130c coupled to an adapter 180 (FIG. 4A) for a video monitor for use on a long term basis by the practitioner or other medical personnel may be used.

Figure 5:
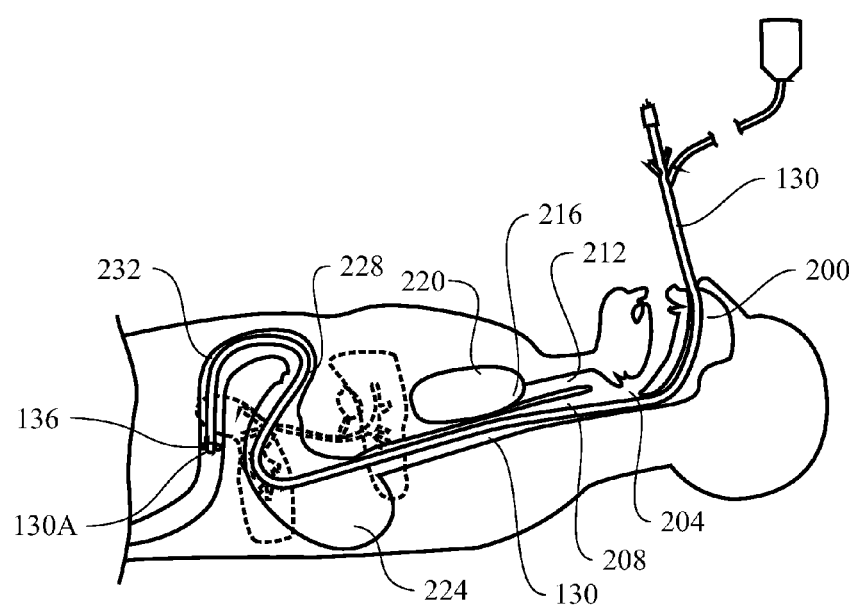
FIG. 5 shows a cross-sectional view of a patient being fed with a nasoenteric feeding tube placed in the person in accordance with principles of the present invention.

With reference to FIG. 5, there is shown a cross-sectional view of a patient (in this case a human although other animals including, but not limited to, horses, cows, pigs and other vertebrates, may be "patients" as well) being fed with a nasoenteric feeding tube placed in the patient in accordance with principles of the present invention. The distal end 130A of the feeding tube 130 is passed through the nasal canal 200 and past the pharynx 204. Care is taken that the distal end 130A advances down the esophagus 208 rather than into the trachea 212 and into the bronchi 216 and lungs 220. Advancing the feeding tube into the trachea, bronchi and lungs can result in numerous medical problems, including damage to the trachea and the bronchi and potentially a puncture of the lungs. Additionally, delivery of feeding solution in the lung can be catastrophic. Thus, the prior art has used a variety of expensive and time consuming procedures to ensure that the feeding tube is positioned properly.

Once placement in the esophagus is confirmed, the distal end 130A of the feeding tube 130 is advanced down into the stomach 224. In some situations, such placement may be acceptable. However to avoid reflux, aspiration and other concerns, it is usually preferred to pass the feeding tube through the pyloric sphincter 228 and into the duodenum 232. Once the distal end 130A is sufficiently into the intestines, the anchoring device 136, such as a balloon, coil or stent, may be deployed, to help hold the feeding tube 130 in place.

Not only is placement of the feeding tube 130 of the present invention safer than blind placement, it is anticipated that the procedure of placing the feeding tube 130 will, on average, take about one-fourth to one-third the amount of time as blind placement, as the practitioner does not have to move as slowly when he or she can verify the location of the distal end 130A of the feeding tube 130. This is in addition to the substantial saving in time by not requiring fluoroscopic, X-ray or other radiological confirmation of placement of the feeding tube. Thus, a patient may be able to begin receiving nutrition or medication within, for example, 20 minutes to half-an-hour instead of 24 hours. Additionally, the present procedure is better than use of an endoscope because the tube does not need to be advanced orally and then pulled back up through the nasal canal, saving both time and discomfort to the patient. Additionally, there is a substantial cost savings as there is no need to re-sterilize an endoscope.

Figure 6A:
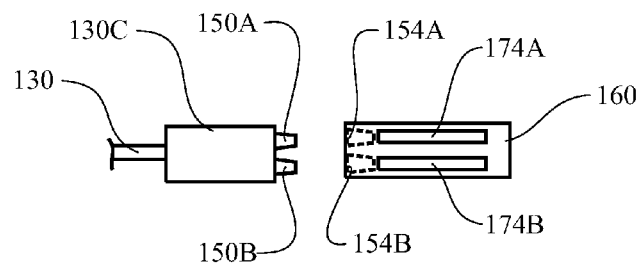
FIG. 6A shows a close-up view of a control unit adapter disposed at or adjacent the proximal end of the feeding tube.

FIG. 6A shows a close-up view of a control unit adapter 130c disposed at or adjacent the proximal end of the feeding tube. Each of the projections 150A and 150B are slightly tapered or conical and are designed to nest in tapered receptacles 154A and 154B reducing the potential for misalignment of the fiber faces. Receptacle 154A is disposed in alignment with a light source 174A and receptacle 154B is disposed in communication with a camera 174B or other image rendering device. In the event that the optical system in the feeding tube included a camera, receptacle 154B typically would be disposed in more direct communication with the display 164. The projection(s) can also be configured to provide for concentric orientation of the fibers.

Figure 6B:
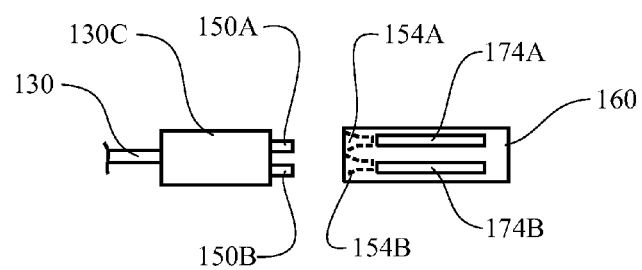
FIG. 6B shows a close-up view of an alternate configuration of a control unit adapter of the feeding tube.

FIG. 6B shows a close-up view of an alternate configuration of a control unit adapter 130c of the feeding tube 130. Rather than tapered projections, the projections 150A and 150B are generally cylindrical, but the receptacles 154A and 154B are tapered. It will be appreciated that numerous different configurations could be used. For example, the projections could also have a squared or rectangular cross-section.

Figure 6C:
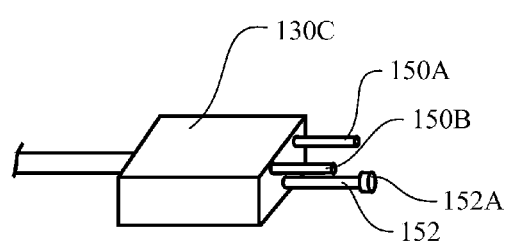
FIG. 6C shows a close-up perspective view of the control unit shown in FIG. 6B.

In FIGS. 6A and 6B, the cable 152 was omitted for clarity. If the feeding tube 130 includes a wire or cable for selectively straightening or curving the distal end of the feeding tube, the control unit 160 will preferably have a steering mechanism. FIG. 6C shows a close-up perspective view of the control unit adapter 130c including the distal end of the cable 152. As shown, the cable includes an engagement member 152A, which may be a ball, a ring, a knob or other mechanism wherein the control unit can engage and hold the wire so that the wire may be pulled away from or pushed toward the distal end of the feeding tube. As will be discussed below, the movement of the wire can bend a straight ended wire, or can straighten a distal end which is preformed with a curve. Such a structure can also be used to deploy a coil anchor as will be discussed below.

Figure 7:
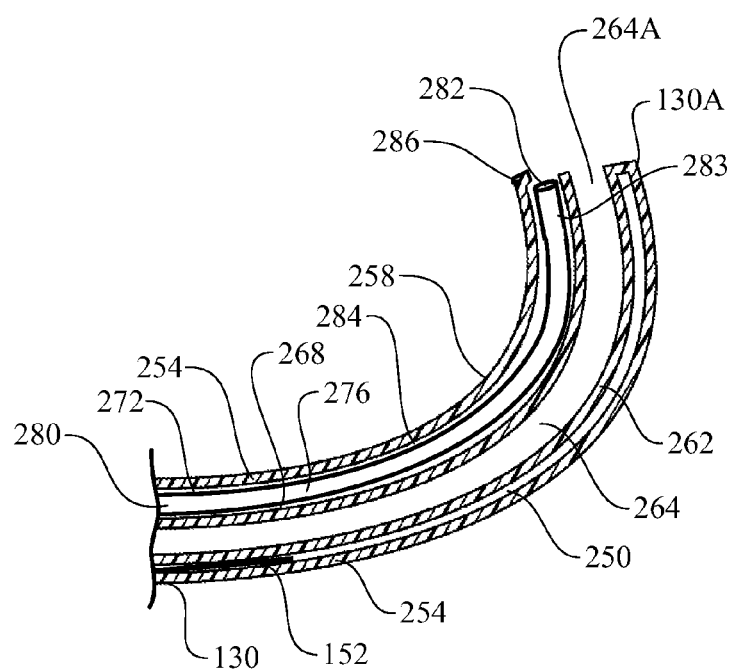
FIG. 7 shows a close-up cross-sectional view of the distal end of a feeding tube made in accordance with principles the present invention wherein the feeding tube can be steered during placement.

Turning now to FIG. 7, there is shown a close-up view of the distal end 130A of the feeding tube 130. The retaining device, such as a balloon, coil, stent, etc., is not shown for clarity, but may be included on such a device. However, the feeding tube may be used without any anchoring mechanism. The distal end 130A is pre-formed with a curvature. The curvature may have a radius of about 2 cm, or could have greater or lesser curvature depending on the desire of the practitioner.

The feeding tube 130 includes a lumen 250 which is typically disposed along the outer wall 254 of the feeding tube opposite the inner curvature 258. The distal end 152B of a cable or wire 152, which may have a resistance to bending which is stronger than the inherent formation of the distal end 130A of the feeding tube 130, is disposed in the lumen 250. As the wire 152 is advanced toward the distal end 130A of the feeding tube, the wire causes the distal end of the feeding tube to straighten. Thus, by advancing or withdrawing the wire 152, the practitioner can control the amount of curvature which is present at the distal end 130A of the feeding tube 130. In the embodiment shown in FIG. 4, this is done by moving the trigger 168. Pulling the trigger 168 will push the wire toward the distal end 130A of the feeding tube 130, straightening the feeding tube, while pushing the trigger 168 forward will withdraw most of the wire 152 and allow additional curvature in the distal end.

Also shown in FIG. 7 is an inner wall 262 which divides the lumen 250 carrying the steering wire 152 from a feeding lumen 264. Typically the feeding lumen 264 will be the largest lumen so as to accommodate the viscosity present in some feeding solutions. The feeding lumen 264 typically ends in an open port 264A at the distal end 130A of the feeding tube 130, while the steering lumen 250 typically will be closed at the distal end.

The feeding lumen 264 is bordered by another wall 268. Wall 268 and the outer wall 254 along the interior side form a third lumen 272 which, as explained below, includes an optical system 276. The optical system 276 may include a plurality of fiber optic fibers, generally shown as a single cable 280 and a lens 282. In the alternative a camera 283 may be disposed adjacent the end of distal end 130A and the cable 280 used to transmit pictures from the camera. While the optical system 276 could fill the entire third lumen 272, a void 284 may be left running along the third lumen which will allow fluid to flow in the lumen along side the optical system 276. (In multiple places in the figures, the optical system is shown with a lens 282 at the end of fiber optics and camera 283. It will be appreciated that these can be in the alternative or could be used in combination.)

The void 284 extending in the third lumen 272 along the optical system 276 allows, a cleaning fluid, such as saline solution or air, to be injected through the third lumen and help clean the lens 282. (If a camera 283 were used waterproofing material could be added if necessary). Directing the cleaning fluid may be done, for example, by a deflecting projection 286 disposed on the outside wall 254. As saline solution or other cleaning fluid is injected through the third lumen 272, the solution is deflected across the lens 282, to thereby clean the lens and provide better visibility. (The use of air can also be advantageous as injecting air inflates the gastrointestinal tract and can make visualization of tissue adjacent the feeding tube easier.)

Figure 8:
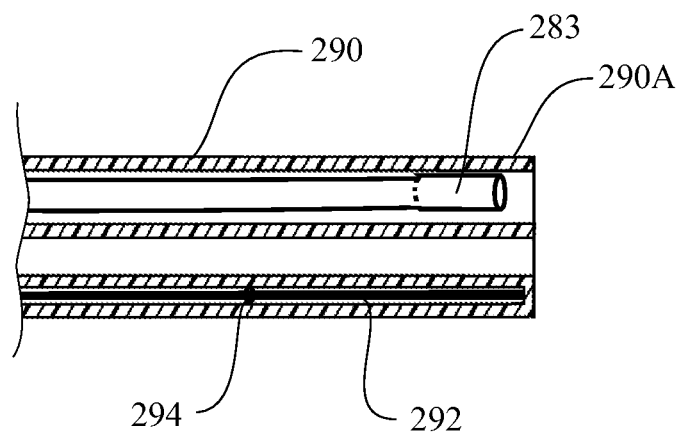
FIG. 8 shows a close-up cross-sectional view of the distal end of a feeding tube made in accordance with the present invention made in accordance with principles of the present invention.

Turning now to FIG. 8, there is shown a close-up, cross-sectional view of the distal end of a feeding tube made in accordance with the present invention made in accordance with principles of the present invention. Unlike feeding tube 130 shown in FIG. 9, the feeding tube 290 shown in FIG. 8 is generally straight. A wire 292 may be attached adjacent the distal end 290A of the catheter. The wire 292 is used to curve the distal end 290A of the feeding tube to assist in steering the feeding tube as it is advanced. This can be accomplished by the wire 292 passing through a neck 294 and is offset such that pulling the wire toward the proximal end of the feeding tube causes the end to defect.

In the alternative, the wire 292 could be formed from a memory shaped material such that the application of a current to the wire causes the distal end of the wire to deflect to thereby turn the distal end 290A of the feeding tube 290.

Figure 9:
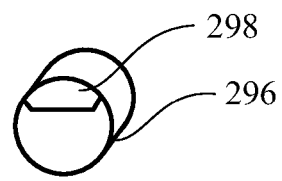
FIG. 9 shows a perspective view of an end cap configured for placement on the distal end of a catheter in order to control fluid flow for cleaning the distal end of the optical system.

Turning now to FIG. 9, there is shown a perspective view of an end cap 296 configured for placement on the distal end of a catheter in order to control fluid flow for cleaning the distal end of the optical system. The end cap 296 includes a deflector projection 298. As with the deflector projection 286 in FIG. 7, the deflector projection 298 is used to direct fluid flow so that when the end cap 286 is attached to the end of the feeding tube, the projection directs fluid flow to the lens on the optical system to thereby clean the optical system of feeding solution or other material.

Figure 10:
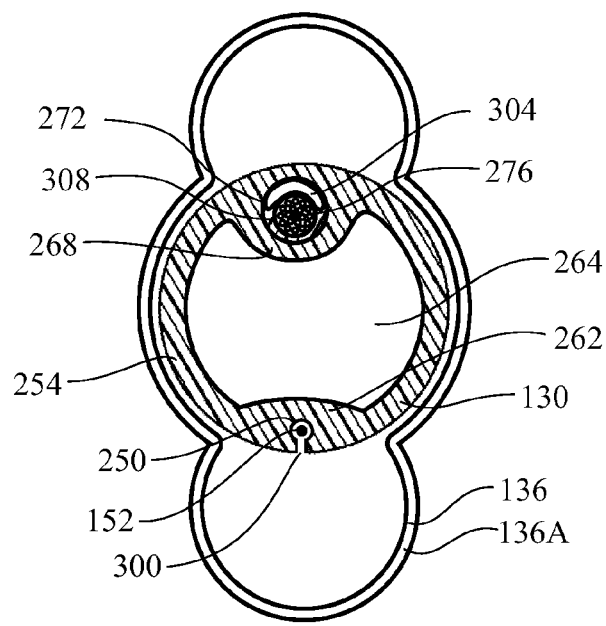
FIG. 10 shows a cross-sectional view of the feeding tube adjacent the distal end with a balloon anchor having been deployed.

FIG. 10 shows a cross-sectional view of the feeding tube 130 adjacent the distal end 130A with an anchoring device 136 with a balloon 136A anchor having been deployed. The balloon 136A is shown as being dual lobed, however it will be appreciated that numerous different designs may be used such as tri-lobed, quad-lobed hour-glass shaped, etc. The anchoring device 136 helps to hold the distal end 130A of the feeding tube 130 at the desired location in the gastrointestinal tract. (It will be appreciated that the balloon will typically be much larger relative to the feeding tube than shown in FIG. 10 when fully inflated.) It is preferred that the anchoring device 136 be multi-lobed so that it does not completely obstruct the intestinal tract, thus allowing gastric fluid to continue to move through the intestinal tract.

FIG. 10 also shows other structures at the distal end 130A of the feeding tube 130. The first lumen 250 may be used not only for the steering wire 152, but also as an inflation lumen if the anchoring device 136 is a balloon 136A. Thus, a small port 300 is provided in the first lumen 250 and extends to the exterior of the outside wall 254.

The second lumen 264 is shown as being substantially larger than the other two. As indicated above, some feeding solutions tend to be somewhat viscous. Having a larger feeding lumen is thus desirable to ensure that the feeding solution may flow through the lumen.

Figure 10A:
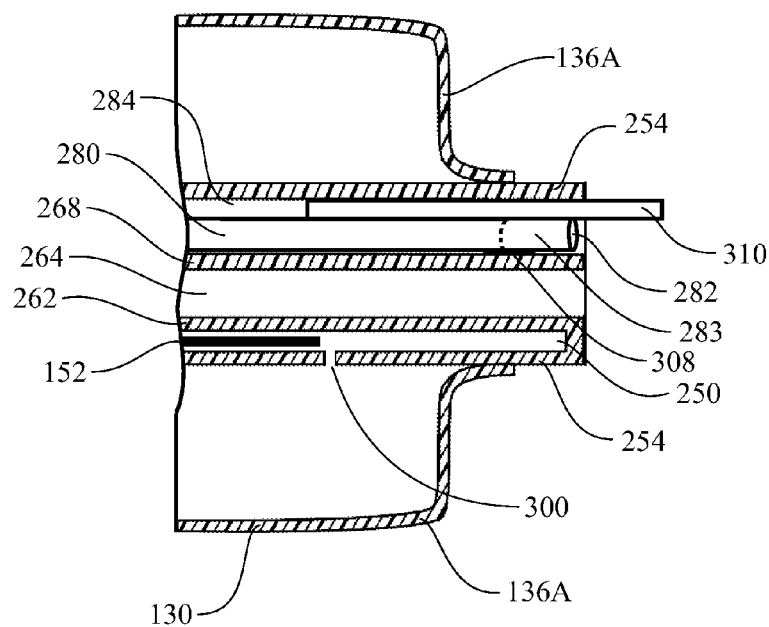
FIG. 10A shows a side cross-sectional view of the distal end of the feeding tube with a sleeve holding the distal end of the optical system in place to form a fluid flow channel within the optical system lumen.

As shown in FIG. 10, wall 268 bounds the top of the second lumen 264 and, with the outer wall 254 bounds the third lumen 272. The third lumen 272 is designed to house the optical system 276 and to provide a port 304 for fluid flow. While the optical system 276 may be left loose in the third lumen 272, it may also be anchored so that a structured port 304 is formed. This can be accomplished, as shown in FIG. 10A, by inserting a sleeve 310 into the third lumen 272 and then injecting a bonding agent 308 to hold the distal end of the optical system 276 in place. This may leave, for example, a generally crescent shaped port 304. When used with some sort of channeling mechanism, such as the deflecting projection 284, the port 304 can assist in cleaning the distal end of the optical system.

FIG. 10A shows a side-cross-sectional view at the same location as the cross-sectional view shown in FIG. 10. The various structures are numbered accordingly. An end cap, such as end cap 296, may be attached to the distal end 130A to assist in cleaning the lens 280.

Figure 11:
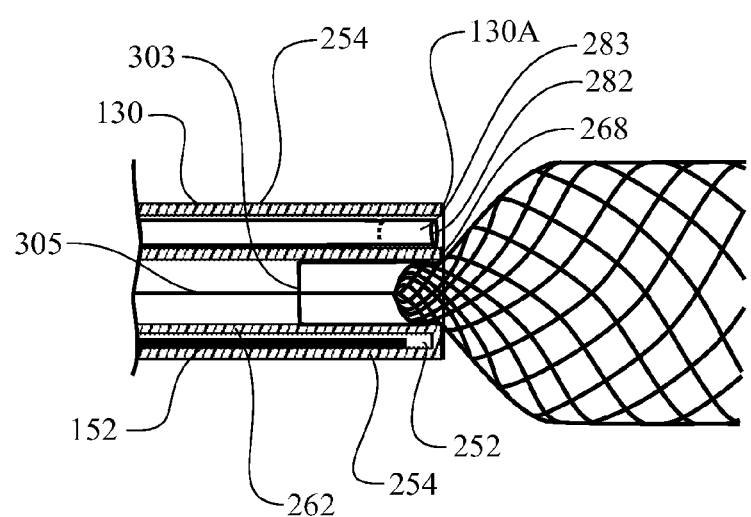
FIG. 11 shows a side cross-sectional view similar to that of FIG. 10A, but with a stent serving as the anchor.

FIG. 11 shows a side-cross sectional view of the feeding tube 130, similar to FIG. 10A. Instead of a balloon 136A for an anchoring mechanism, a stent 136b, such as a wall stent, is used. The stent 136B may be carried in a hypotube 303 and be connected to a wire 305. When the feeding tube 130 is properly positioned in the small bowel, the wire 305 is advanced to push the stent 136B at least partially out of the hypotube. The distal portion of the stent 136B springs open and engages the sides of the small bowel, thereby holding the feeding tube in place.

Figure 12:
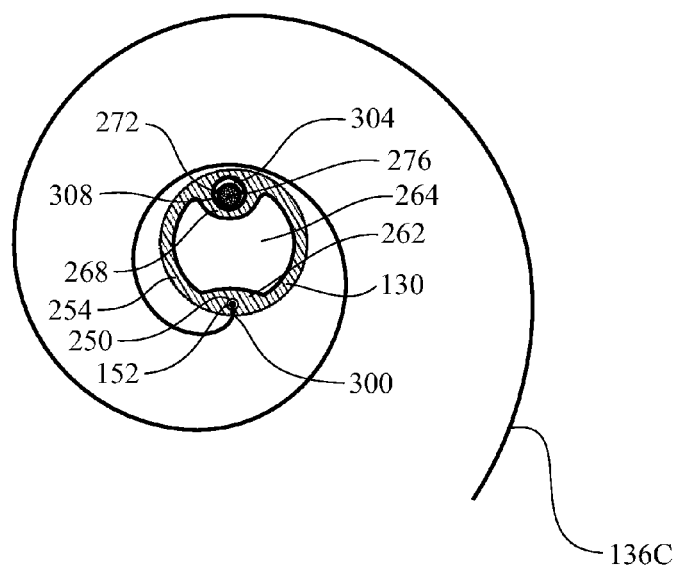
FIG. 12 shows an end view of the distal end of a feeding tube in accordance with the principles of the present invention wherein a coil 136C anchor is disposed to help anchor the distal end of the feeding tube.

Turning now to FIG. 12, there is shown an end view similar to that shown in FIG. 10. Instead of using a balloon 136A (FIG. 10) as the anchoring device 136, the anchoring device 136 is shown in the form of a helical coil 136c. The Stent 136 may be disposed about the exterior wall 254 of the feeding tube 130, or may be carried on the distal end 130A end of feeding tube. When the distal end 130A of the feeding tube 130 is in the desired location, the coil 136c stent may be activated.

Figure 12A:
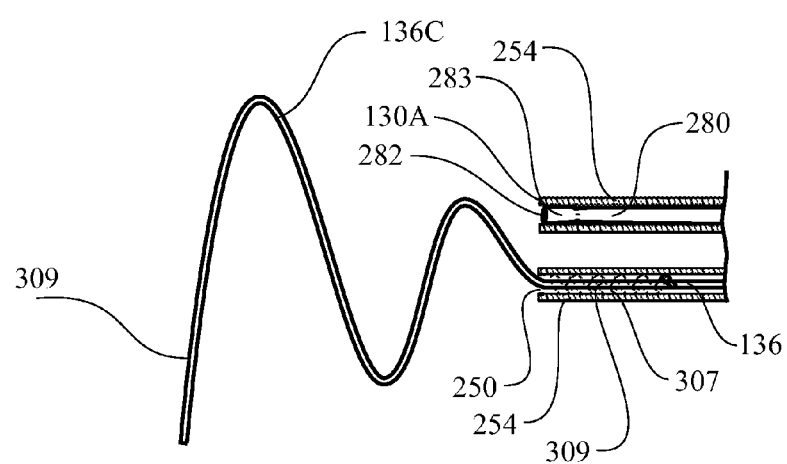
FIG. 12A shows a side cross-sectional view of the feeding tube with a coil serving as the anchor instead of a balloon or stent.

FIG. 12A shows a side view of the feeding tube 130 with the coil 136c deployed. During placement the coil 136c will typically be disposed in one of the lumens. It could be used, for example, in the lumen 250 to act as a stiffener to keep the distal end 130A of the feeding tube 130 from bending when the coil is tightly wound as shown by dashed lines 307. Moving the coil 307 proximally would allow the distal end 130A of the feeding tube 130 to curve for steering during placement. In the alternative, a stiffened section 309 could be placed distally or proximally from the coil 136. Once the distal end 130A of the feeding tube 130 is properly placed, the wire is advanced and the coil 136c is released, allowing it to spring open. The coil 136c itself may hold the distal end of the feeding tube fairly straight depending on how it engaged the intestinal wall, or stiffened portion 309b could be used for that purposed. While many materials could be used for the coil 136c a currently preferred material is nitinol.

Figure 13:
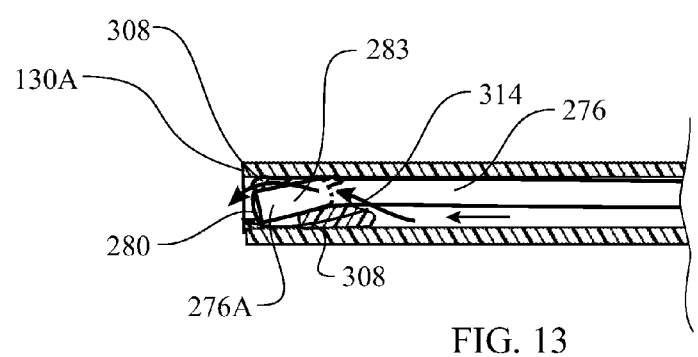
FIG. 13 shows a side cross-sectional view of an optical system/fluid lumen wherein the optical system is deflected to give a more centralized view of the tissue disposed beyond the distal end of the feeding tube.

FIG. 13 shows a side cross-sectional view of an optical system/fluid lumen 272 (the remaining lumens discussed above are omitted for clarity). The distal end 130A of the feeding tube is in contact with both the feeding solution which is gravity fed or pumped into the gastrointestinal tract and with bodily fluids such as bile, etc. To this end, and because the optical system 276 may be left in place over a prolonged period of time, it may be desirable to have the lens 280 recessed from the end of the feeding tube. This protects the lens 280. (Unlike typical endoscopes, the focusing lens 280 may be the only lens provided). While a protective lens is typically disposed at the distal end of an endoscope, such a lens could inhibit the use of the third lumen 272 both for the optical system and for solution injection to flush the lens.

Recessing the lens 280, the relative size of the feeding lumen 264, and disposal of the optical system 276 on one side of the feeding tube complicates the ability of the optical system to see the tissue adjacent the distal end 130A of the feeding tube 130 on both sides of the feeding tube. To overcome these limitations, the distal end 276A of the optical system 276 may be anchored so that the distal end of the optical system is deflected. The deflection may be anywhere from 5 degrees to 40, although 15-25 degrees toward the central long axis of the feeding tube 130 is preferred. The bonding agent 308 used to anchor the distal end 276A of the optical system 276 can be disposed both above and below the distal end 276A to obtain the proper angle, while voids are left to allow fluid flow, represented by arrows 314, around the bonding agent and over the lens 280 to clean the lens.

Figure 14:
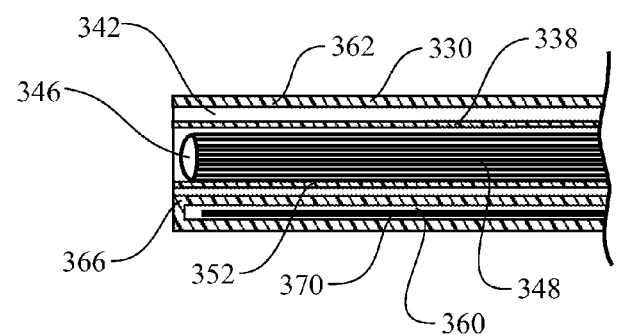
FIG. 14 shows an alternate embodiment of a feeding tube wherein the optical system is disposed in the feeding lumen for insertion or periodic observation, but which is withdrawn for feeding.

FIG. 14 shows an alternate embodiment of a feeding tube 330 made in accordance with one aspect of the present invention. Rather than have an embedded optical system 276 as discussed above, the optical system 334 is disposed in a catheter 338 which is removably disposed in a feeding lumen 342 similar to the second lumen 264 discussed above. The optical system includes a lens 346 and a plurality of optical fibers 348 surrounded by an outer wall or coating 352.

The feeding tube 330 may also include a steering lumen 360 which may be formed by an outer wall 362 of the feeding tube 330 and an inner wall 366. A steering wire 370 disposed in the steering lumen 360 can be used as described above.

The use of the feeding tube 330 is different from the use of the feeding tube 130 described above in that the optical system is removable. As the feeding tube 330 is advanced through the nasal canal, the esophagus, the stomach and the pyloric sphincter, the practitioner can view the tissues adjacent the distal end of the feeding tube on an image viewer, such as the display screen 164 of the control unit 160. Likewise, the steering wire 370 could be controlled by the control unit 160.

Once the feeding tube 330 is in place and optically confirmed, the control unit 160 can be detached and the optical system 338 can be withdrawn. With the optical system 338 withdrawn, the lumen 342 can then be used for introducing feeding solution and/or medicated solution to the patient. The optical system 338 is much less expensive than the use of an endoscope and can be either discarded or may be re-sterilized for subsequent use. If further viewing of the gastrointestinal tract is desired, the optical system 338 can be reinserted. Typically this will be done after flushing the feeding lumen 342 to clear out any feeding solution which may cloud the lens.

The feeding tube 330 is less advantageous than those discussed previously in that it does not allow viewing of the gastrointestinal tract without reinsertion of the optical system 338. However, an advantage is obtained in that the feeding tube 330 can be kept relatively small, thereby making the feeding tube 330 less discomforting to the patient and, in some situations, easier to place.

Figure 15:
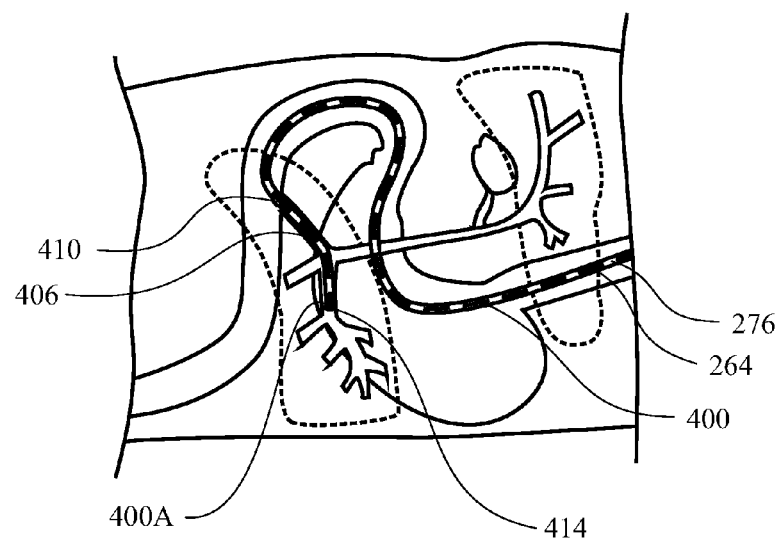
FIG. 15 shows an embodiment of a catheter having an optical system and a drainage port, with the distal end of the catheter being disposed in the pancreatic duct so as to enable visualization of the pancreas and drainage of fluids therefrom.

Turning now to FIG. 15, there is shown an embodiment of a catheter 400 in accordance with another aspect of the present invention. While not shown in FIG. 15, the catheter has an optical system formed therein, and may be structurally very similar to the feeding tube 130. The optical system enables a practitioner to view other portions of the gastrointestinal tract, such as the pancreatic duct or the common bile duct. The catheter 400 may be structurally different from the feeding tube 130 in that it may include a port 410 disposed in communication with a port 414 at the distal end of the catheter to shunt fluid through a restricted duct. The port 410 could be the proximal end of a lumen, or the lumen could extend to the proximal end of the catheter to allow the introduction or withdrawal of fluids therethrough.

When a person is suffering from pancreatitis or an inflamed common bile duct, it is common to place a stent or shunt in the pancreatic duct or the common bile duct to ensure proper drainage of bile or puss or other fluids which need to pass through the gastrointestinal tract. Typically the stent or shunt is placed, left in place for a time and then removed once the symptoms appear to subside.

The catheter 400 of the present invention allows the practitioner to use the optical system not only to place the catheter, but also to observe the tissue for a prolonged period of time. Thus, as shown in FIG. 15, the distal end 400A of the catheter is disposed in the pancreatic duct 406. Puss from an infected pancreas can pass into distal port 414 and drain through a drainage port 410 similar to a shunt. Over a period of time, the practitioner can observe the pancreatic duct to determine how well the pancreatitis is healing and can determine when assisted shunting of fluid from the pancreas is no longer needed. The same procedure could be used with the common bile duct or other structures along the gastrointestinal tract.

In use, a practitioner may insert the catheter 400 in the nasal canal of the patient. (While oral insertion can be used, one advantage of the present invention is the ability to advance through the nasal canal and avoid the complications of oral insertion). Using the optical system the practitioner can advance the catheter down the esophagus, through the stomach, through the pyloric sphincter. The catheter 400 is then turned and advanced into the pancreatic duct, the common bile duct or other structure which the practitioner needs to observe. While the catheter is left in place, the lumen between ports 414 and 410 allows gastrointestinal fluid, puss, etc. to drain. The practitioner can monitor the condition of the tissue adjacent the distal end 400A of the catheter and confirm if the patient's condition is improving. Once the catheter is no longer needed, it can be conveniently withdrawn. In contrast, a shunt or stent typically requires the reinsertion of an endoscope, or the use of fluoroscopy, etc. to withdraw the stent or shunt.

The teachings of the present invention can be applied to other fields. For example, catheters which are left in place can be provided with an optical system as disclosed. A practitioner can use the optical system to monitor internal tissue over a prolonged period of time without the need for reinsertion of an endoscope, etc.

Figure 16:
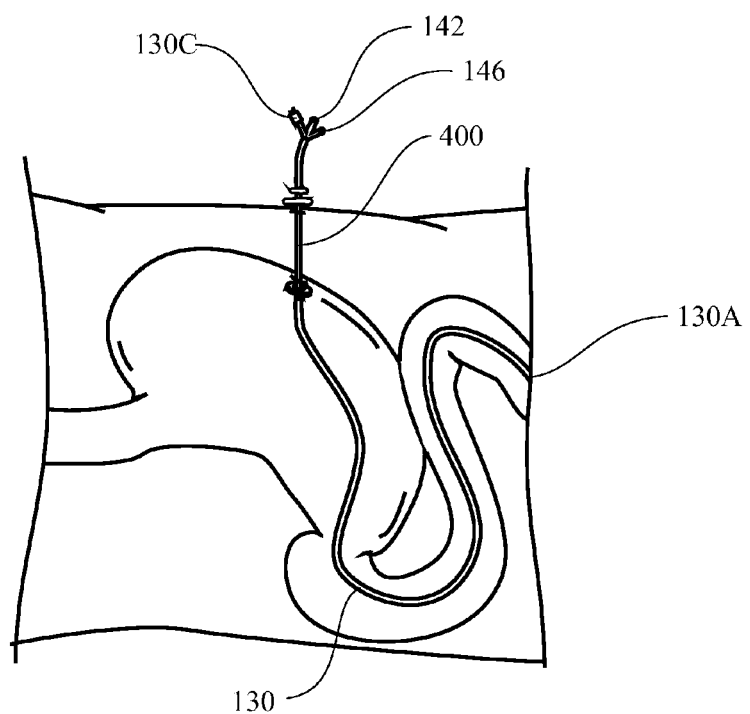
FIG. 16 shows a feeding tube formed in accordance with the principles of the present invention used as a jejunual extension tube in percutaneous gastrojejunal feeding tubes (PEGJ).

FIG. 16 shows yet another aspect of the invention. Rather than serving as a nasoenteric feeding tube, the feeding tube 130 is advanced through a percutaneous gastrojejunal feeding tube (PEGJ) to form a jejunual extension tube. Presently for PEGJ tubes the jejunal extension tube is threaded through the existing gastrostomy tube or stoma into the small bowel. This is done using fluoroscopy or endoscopy to advance a wire into the small intestine and then a jejunal feeding tube is passed over the wire into the small intestine (jejunum). In contrast, the feeding tube 130 of the present invention provides direct visualization and may include a steering mechanism could perform the same task without the drawbacks of using endoscopy or fluoroscopy as noted previously.

In use, the distal end 136A is passed through the gastostomy tube 400 in the patient's abdomen. With the control unit attached, the practitioner can observe the stomach and readily find the pyloric sphincter. The distal end 136A is advanced by pushing on the feeding tube 130 until the distal end has passed the pyloric sphincter a desired distance. An anchoring device (not shown) can then be deployed if desired help hold the feeding tube in place.

While a guidewire may be used if desired, it is generally not necessary. Additionally the cost of using an endoscope is eliminated and there is no need for confirmation of placement by use of X-ray or fluoroscopy. Additionally, the procedure of advancing the feeding tube is less time consuming and may be done by a practitioner with relatively little training.

One major advantage of the present invention is that it allows for more rapid and safer placement of a feeding tube. Additionally it avoid expensive X-rays and fluoroscopy and reduces the amount of radiation that the patient is exposed to. Another major adjacent is that it removes the need for the procedure to be done in a hospital. For example, if a patient in a nursing home has difficulty holding down food, the patient will typically be taken to a hospital where the feeding tube may be inserted—the majority being done blind. Just the time and expense of getting the patient to the hospital is disadvantageous. Additionally, the patient must undergo the procedure and be subject to radiation or other unpleasant procedures to confirm placement of the feeding tube. In the 24-48 hours that may have transpired since the patient was first diagnosed as likely needing a feeding tube, the patient may have received no food or needed medication.

A significant advance of the present invention is that placement can be done with relatively little training and need not be done in a hospital. By carefully observing the tissue, a practitioner can steer away from the trachea and ensure that the feeding tube is properly descending in the esophagus. The feeding tube can then be advanced until the practitioner is certain that the distal end of the feeding tube is a desired distance past the pyloric sphincter and then the procedure is done. The procedure may take as little as 5 to 10 minutes and could be done right at the bedside of a nursing home patient instead of at the hospital. Instead of waiting 24 hours or more for nutrition, feeding could commence in under half and hour. Additionally, there would be a substantial savings in cost and manpower by not having to transport the patient to the hospital.

Likewise, the feeding tube 130 of the present invention could be used in a variety of other situations, such as pediatric and other clinical settings or in post operative situations where the patient is having trouble keeping down food. With a relatively short and simple procedure, nutrition can be delivered directly into the intestines of the patient. Thus, it is anticipated that substantial cost savings may be achieved at the same time making the entire procedure less straining on both the patient and the practitioner.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. For example, while aspects of the present invention do not require an intubation tube or guidewire, there is nothing which would prevent oral insertion or the use of a guidewire with a device of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for draining fluid in the gastrointestinal tract, the method comprising:
    selecting a catheter having a distal end, a first port disposed in the distal end and a second port disposed proximal from the distal end and in fluid communication with the first port, and an optical system extending substantially the length of the catheter;
    advancing the catheter through the nasal canal, the esophagus and the stomach while at least periodically observing images relayed by the optical system; and
    advancing the distal end of the catheter into a duct of the gastrointestinal system such that the second port is disposed in the intestine so as to allow fluid to drain through the lumen extending from the first port to the second port.

2. The method according to claim 1, wherein the catheter is left in place more than 24 hours and wherein the method comprises periodically viewing tissue and/or fluid in the duct through the optical system.

3. The method of claim 1, wherein the duct is a pancreatic duct.

4. The method of claim 1, wherein the duct is a common bile duct.

5. The method of claim 1, further comprising draining fluid through the second port and into the intestine.

6. An optically guidable feeding tube comprising:
    a tube comprising an elongate body, the elongate body being of sufficient length that the proximal end may be disposed outside of a patient adjacent a nasal or oral cavity of the patient while the elongate body extends through the nasal or oral cavity of the patient, though the patient's esophagus and at least into the stomach, the elongate body including at least one lumen having an opening through the distal end, the lumen configured for passing a feeding solution therethrough;
    an optical system disposed within the elongate body comprising a lighting structure for conveying light for lighting tissue adjacent the distal end of the elongate body and an image transmitting structure for conveying images of tissue adjacent the distal end of the elongate body, the optical system being mounted in the elongate body so as to remain in the elongate body during use of the tube;
    wherein the optical system is disposed in a lumen having an open distal end and wherein the optical system has a distal end which is fixedly disposed at an angle of between about 15 and 25 degrees relative to a central long axis of the tube at the distal end.

7. The optically guidable feeding tube of claim 6, wherein the optical system comprises a camera.

8. The optically guidable feeding tube of claim 6, wherein the optical system comprises a plurality of fiber optic fibers and a lens attached to the fiber optic fibers.

9. The optically guidable feeding tube of claim 6, further comprising an anchoring device attached to the tube adjacent the distal end thereof for anchoring the tube in the gastrointestinal tract, wherein the anchoring device is shaped to not occlude gastrointestinal tract passages such that gastric fluid within the gastrointestinal tract is able to flow past the anchoring device when the tube is anchored.

10. The optically guidable feeding tube of claim 9, wherein the anchoring device comprises a multi-lobe balloon.

11. The optically guidable feeding tube of claim 9, wherein the anchoring device comprises a stent attached to the distal end of the feeding tube.

12. The optically guidable feeding tube of claim 9, wherein the anchoring device is a coil.

13. The optically guidable feeding tube of claim 6, wherein the elongate body has an outer wall and wherein the optical system is formed into the outer wall at a plurality of locations spaced about the outer wall.

* * * * *